United States Patent
Kwak et al.

(10) Patent No.: US 6,491,955 B1
(45) Date of Patent: Dec. 10, 2002

(54) β-D-GALACTOSIDASE MICROENCAPSULATED WITH FATTY ACID ESTER AND MILK CONTAINING THE SAME

(75) Inventors: Hae-Soo Kwak, Seoul (KR); Mi-Ri Lim, Seoul (KR)

(73) Assignee: Anigen Co., Ltd. (KR)

( * ) Notice: Subject to any disclaimer, the term of this patent is extended or adjusted under 35 U.S.C. 154(b) by 0 days.

(21) Appl. No.: 09/564,994

(22) Filed: May 4, 2000

Related U.S. Application Data

(63) Continuation of application No. 09/122,119, filed on Jul. 24, 1998, now abandoned.

(30) Foreign Application Priority Data

Feb. 24, 1998 (KR) .............................................. 98-5802

(51) Int. Cl.[7] .................................................. A23C 9/12
(52) U.S. Cl. ............................ 426/61; 426/34; 426/89; 426/99; 426/580; 426/585
(58) Field of Search ........................ 426/61, 580, 585, 426/34, 48, 64, 89, 98, 99

(56) References Cited

U.S. PATENT DOCUMENTS

| | | | |
|---|---|---|---|
| 5,064,669 A | 11/1991 | Tan et al. | 426/307 |
| 5,391,371 A | 2/1995 | Jacobson et al. | 424/94.2 |
| 5,902,617 A | 5/1999 | Pabst | 426/61 |
| 6,402,997 B1 | 6/2002 | Kwak et al. | |

OTHER PUBLICATIONS

Rao et al., AN 436073 FROSTI, abstracting Food Science and Technology International, 1997, Apr. 3(2), 81–86, Apr., 1997.
Rao et al., AN 381960 FROSTI, abstracting Journal of Food Biochemistry, 1995 18(4), 239–252, 1995.
Chawan et al. AN 327212 FROSTI, abstracting Journal of Food Biochemistry, 1993, 16(6), 349–357, 1993.
C.B, Chawan P.K. Penmetsa, R. Veeramachaneni, D.R. Rao, "Liposomal Encapsulation of B–Galactosidase: Effect of Buffer Molrity, Lipid Composition and Stability in Milk," Journal of Food Biochemistry 16 (1993) 349–357.
D.R. Rao, C.B. Chawan, R. Veeramachaneni, "Liposomal Encapsulation of B–Galactosidase: Comparison of Two Methods of Encapsulation and In Vitro Lactose Digestibility," Journal of Food Biochemistry 18 (1995) 239–251.

*Primary Examiner*—Leslie Wong
(74) *Attorney, Agent, or Firm*—Mathews, Collins, Shepherd & McKay, P.A.

(57) ABSTRACT

A β-D-galactosidase which is encapsulated with fatty acid ester, does not exert its hydrolysis function in milk but hydrolyze lactose in the human body. Hence, the milk containing the encapsulated β-D-galactosidase, does not change in sweetness with storage and is digestible to the β-D-galactosidase-deficient people. In addition, the milk can maintain its characteristic taste without off-flavor by virtue of the excellent feature of fatty acid ester.

6 Claims, No Drawings

β-D-GALACTOSIDASE MICROENCAPSULATED WITH FATTY ACID ESTER AND MILK CONTAINING THE SAME

This application is a continuation of U.S. patent application Ser. No. 09/122,119 filed Jul. 24, 1998, now abandoned.

BACKGROUND OF THE INVENTION

1. Field of the Invention

The present invention relates to a fatty acid ester-microencapsulated β-D-galactosidase and milk containing the same. More particularly, the present invention relates to easy digestion of milk by adding β-D-galactosidase microencapsulated with fatty acid ester.

2. Description of the Prior Art

In milk, lactose is contained at an amount of about 4.8–5.2%. After ingestion of milk, lactose is hydrolyzed to galactose and glucose, which are both well absorbed in the small intestine, by β-D-galactosidase an enzyme produced in the small intestine. Nearly all infants and children are able to digest lactose. In contrast, a majority of adults in certain population groups are deficient in β-D-galactosidase, which makes them intolerant of milk. In a β-D-galactosidase-deficient adult, lactose accumulates in the lumen of the small intestine after ingestion of milk because there is no mechanism for the uptake of this disaccharide. The large osmotic effect of the unabsorbed lactose leads to an influx of fluid into the small intestine. At the caecum, the unabsorbed lactose is fermented to organic acids by the enteric bacteria. Hence, the clinical symptoms of lactose intolerance are abdominal distention, nausea, cramping, pain, and watery diarrhea. β-D-galactosidase deficiency, whose reason is not clearly revealed, appears to be inherited and postnatal. The prevalence of β-D-galactosidase deficiency in human populations varies greatly. For example, 3% of Danes are deficient in β-D-galactosidase, compared with 97% of Thais and 84% of Koreans. About two-thirds of the population the world over are reported to be problematic in digesting milk. The adults deficient in β-D-galactosidase are reluctant to take milk. It is nutritiously beneficial, particularly, in an aspect of calcium metabolism, for older people to ingest milk, but most of them do not ingest the recommended daily amount (500 ml/day).

In order to help the lactose of milk ve digested and well absorbed in the body, β-D-galactosidase would be added to the milk. However, the glucose and galactose resulting from the hydrolysis action of the enzyme makes the milk too sweet for the consumers to drink. Hence, it is necessary that the β-D-galactosidase added be designed to hydrolyze the lactose only after ingestion of milk.

Conventionally, the lactose content of milk is lowered by adding β3-D-galactosidase or immobilized β-D-galactosidase to milk during milk processing to hydrolyze the disaccharide to the monosaccharides (Am. J. Gastroenterol. 83, 1145 (1988); Am. J. Clin. Nutr. 32, 1989 91979); Am. J. Clin. Nutr. 41, 222 (1985); U.S. Pat. No. 1,350,003). The lactose-hydrolyzed milk produced by these techniques, however, is much higher in sweetness than general milk, so it is not so suitable to drink.

In 1980s, to avoid this problem, milk was sold together with a pack of powdered β-D-galactosidase in U.S.A. Men or women who are troubled in digesting milk could take the powdered enzyme upon ingestion of milk. Preventive as it is of increasing the sweetness of milk, this effort is very cumbersome to the consumers.

In 1990s, a further advanced milk product was developed. The milk was free of lactose because it was removed through ultra filtration (UF). However, removal of lactose is accompanied by a great loss of an important nutrient as well as of milk's characteristic flavor. Also, this technique has a significant disadvantage of decreasing the product yield by 5%. In addition, the UF apparatus is very expensive and continuously needs supplies, such as filters, cleansing agent, etc, giving rise to a significant increase of cost.

An advanced technique is disclosed in Korean Pat. Nos. 088464 and 088465. According to the patents, butter is melted at 40° C. for 6 hours, dispersed at 50° C. by use of the supernatant fat, emulsified with the aid of an emulsifying agent, and sprayed under a high pressure into low-pat milk (pat content 1% or less) at 5–10° C. to coat lactose. As a result, capsules 5–20 μm in diameter are produced at a yield of about 85%. For its preparation, the emulsion requires a long time and a high temperature (50° C.), which may be factors to cause degradation in the production yield and in the quality of the fat, respectively. Further, since fat is used as the coating agent, low-fat milk is needed, requiring a cream separation process. In addition, the emulsifying agent used generally smells bad, giving unpleasant flavor to the milk. Furthermore, the capsules are too large in diameter and so rise to the surface of milk after storage for 2–5 hours.

SUMMARY OF THE INVENTION

Therefore, it is an object of the present invention to overcome the above problems encountered in prior arts and to provide a β-D-galactosidase which does not exert its hydrolysis function in milk but hydrolyze lactose in the human body.

It is another object of the present invention to provide milk which does not change in sweetness with storage and is digestible to the β-D-galactosidase-deficient people.

It is a further object of the present invention to provide milk which maintains its characteristic taste without off-flavor.

In accordance with an aspect of the present invention, there is provided a β-D-galactosidase encapsulated with fatty acid ester.

In accordance with another aspect of the present invention, there is provided milk which contains the β-D-galactosidase encapsulated with fatty acid ester.

In the present invention, medium chain triglyceride (MCT), decaglycerin monostearate (PGMS) or a combination thereof is used as a coating agent to encapsulate β-D-galactosidase. It is preferable that the production yield of the micro-encapsulated β-D-galactosidase is measured to obtain an optimal condition for encapsulation. The influence of the microencapsulated β-D-galactosidase on the taste and odor of the milk is investigated through functional tests and its medicinal effect is examined through a clinical demonstration in which milk-intolerant persons drink the milk containing the microencapsulated β-D-galactosidase and their clinical symptoms are monitored.

DETAILED DESCRIPTION OF THE PREFERRED EMBODIMENTS

Fatty acid ester, used as food additive, is non-toxic, tasteless, and odorless. In accordance with the present invention, fatty acid ester is used as a coating agent to encapsulate lactose. Use of fatty acid ester is very advantageous in many aspects. First, the time and temperature needed in preparing the emulsion can be significantly reduced. In addition, it is unnecessary to subject milk to cream separation since no fat is added. No additional emulsifying agent is needed. Further, capsules can be produced at a yield of at least 95% with a diameter of 2–3 μm. These microcapsules are uniformly dispersed in milk and do not change for the term of validity of milk (about 10 days). The milk containing the encapsulated lactose gives no off-flavor and is similar in sweetness and general flavor to typical milk.

MCT and PGMS are used as coating agents in the present invention. β-D-galactosidase is mixed with MCT and/or PGMS and the mixture is sprayed and centrifuged to confine the β-D-glactosidase to microcapsules. The production yield of the micro-encapsulated β-D-galactosidase is calculated by measuring the activity of the β-D-galactosidase which is not encapsulated in the spray.

The microencapsulated β-D-galactosidase is added to milk which is, then, subjected to functional tests for flavor and off-flavor and to clinical demonstration to milk-intolerant patients.

A better understanding of the present invention may be obtained through the following examples which are set forth to illustrate, but are not to be construed as the limit of the present invention.

EXAMPLE I

Micro-Encapsulation of β-D-Galactosidase with MCT and Yield

MCT and β-D-glactosidase were mixed at a ratio of 20:1, 15:1, 10:1, and 5:1 and stirred at a speed of 1200 rpm for 1 min. The resulting mixtures were each sprayed with the aid of a spray gun to a dispersion containing 0.05% Tween-60 at 5° C. and then, centrifuged at 4,500×g. The supernatants each were mixed with an equal volume of the dispersion and centrifuged. This procedure was carried out twice to prepare microcapsules.

The yield of the micro-encapsulated β-D-galactosidase was measured through an indirect method in which the activity of the β-D-galactosidase which is not capsulated within the spraying solution but present in an external solution, is measured. The results are given in Table 1, below.

TABLE 1

Yields of micro-encapsulated β-D-galactosidase According to the weight ratio of MCT to Enzyme

| % (W/W) | | |
|---|---|---|
| MCT | β-D-Galactosidase | Yield (%) |
| 20 | 1 | 97.6 |
| 15 | 1 | 94.9 |
| 10 | 1 | 74.7 |
| 5 | 1 | 61.8 |

As apparent from the data, the yield is the highest when the ratio of the MCT: β-D-galactosidase is 20:1 and decreases as the ratio decreases.

EXAMPLE II

Micro-Encapsulation of β-D-Galactosidase with PGMS and Yield

PGMS is highly viscous and in a solid state at room temperature. After being heated to 55° C. to reduce its viscosity, PGMS was diluted with distilled water (PGMS:water 5:4), mixed together, allowed to stand for 20 min, and stirred at 1,200 rpm for 1 min to give a sprayable solution. This solution and β-D-galactosidase were mixed at a ratio of 20:1, 15:1, 10:1, and 5:1 and heated to 55° C. while stirring at 1,200 rpm for 30 sec. The resulting mixtures were each sprayed with the aid of a spray gun to a dispersion containing 0.05% Tween-60 at 5° C. and then, centrifuged at 25,000×g. The supernatants each were mixed with an equal volume of the dispersion and centrifuged. This procedure was carried out twice to prepare microcapsules.

The yield of the micro-encapsulated β-D-galactosidase was measured in the same manner as in Example I. The results are given in Table 2, below.

TABLE 2

Yields of Micro-Encapsulated β-D-galactosidase According to the Weight Ratio of PGMS to Enzyme

| % (W/W) | | |
|---|---|---|
| PGMS* | β-D-Galactosidase | Yield (%) |
| 20 | 1 | 65.9 |
| 15 | 1 | 72.8 |
| 10 | 1 | 64.9 |
| 5 | 1 | 50.9 |

*diluted PGMS (PGMS:water 5:4)

As apparent from the data, the yield is the highest when the ratio of the PGMS: β-D-galactosidase is 15:1 and the next when 20:1. The lower yields than those of Example I were attributed to the use of much distilled water.

EXAMPLE III

Micro-Encapsulation of β-D-Galactosidase with a Combination of MCT and PGMS and Yield MCT is inexpensive but somewhat poor in quality while PGMS is expensive but excellent in quality. A combination of these two coating agents was used to prepare microcapsules. First, a diluted PGMS in which PGMS is mixed with distilled water (5:4), was mixed with MCT at a ratio of 5:5.

This solution and β-D-galactosidase were mixed at a ratio of 20:1, 15:1, 10:1, and 5:1 and stirred at 1,200 rpm for 1 min. β-D-Galactosidase was encapsulated in the similar manner to that of Example I.

The yield of the micro-encapsulated β-D-galactosidase was measured in the same manner as in Example I. The results are given in Table 3, below.

TABLE 3

Yields of micro-encapsulated β-D-galactosidase According to the weight ratio of a Combination of MCT and PGMS to Enzyme

| % (W/W) | | Yield |
|---|---|---|
| MCT + PGMS[1] | β-D-Galactosidase | (%) |
| 20 | 1 | 92.2 |
| 15 | 1 | 94.5 |
| 10 | 1 | 69.8 |
| 5 | 1 | 55.6 |

[1]MCT:PGMS (diluted PGMS, PGMS:water 5:4) 5:5

As apparent from the data, the yield is the highest when the ratio of the coating agent: β-D-galactosidase is 15:1 and the next highest when 20:1.

EXAMPLE IV

Functional Test for Sweet Taste of the Milk Containing β-D-Galactosidase Micro-Encapsulated with Each of MCT and PGMS The β-D-galactosidases which were Micro-encapsulated with MCT in Example I and with PGMS in Example II, each was added to milk at an amount of 60 ppm and the milk was stored at 5° C. for 5 days. The sweet taste of the milk was compared with that of general milk. The results are given in Table 4, below. As shown in Table 4, 18 persons answered "the same as in general milk" and 2 persons "a little sweeter than general milk" for the MCT-treated milk, while 10 persons answered "the same as in general milk" and one person "a little sweeter" for the PGMS-treated milk.

TABLE 4

Functional Test for Sweet Taste of Milk added with MCT-or PGMS-encapsulated β-D-Galactosidase

| Sweetness (Compared with General Milk) | Examinees[1] Milk with Microencapsulated Enz. | |
|---|---|---|
| | MCT | PGMS |
| The Same | 18 | 19 |
| A little Sweeter | 2 | 1 |
| Moderately Sweeter | 0 | 0 |
| Considerably Sweeter | 0 | 0 |
| Much Sweeter | 0 | 0 |

[1]20 persons in total

EXAMPLE V

Functional Test for Sweet Taste of the Milk Containing β-D-Galactosidase Micro-Encapsulated with a Combination of MCT and PGMS The β-D-galactosidase which was micro-encapsulated with a combination of MCT and PGMS in Example III, was added to milk at an amount of 60 ppm and the milk was stored at 5° C. for 5 days. The sweet taste of the milk was compared with that of general milk. The result is given in Table 5, below. As shown in Table 4, 19 persons answered "the same as in general milk" while only one person "a little sweeter than general milk". This result was the same as that for the PGMS-treated milk.

TABLE 5

Functional Test for Sweet taste of Milk Containing the β-D-Galactosidase microencapsulated with a combination of MCT and PGMS.

| Sweetness (compared with General Milk) | Examinees[1] Milk with Microencapsulated Enz. MCT + PGMS |
|---|---|
| The Same | 19 |
| A little Sweeter | 1 |
| Moderately Sweeter | 0 |
| Considerably Sweeter | 0 |
| Much Sweeter | 0 |

[1]20 persons in total

EXAMPLE VI

Functional Test for Off-Flavor of Milk Containing β-D-Galactosidase Micro-Encapsulated with Each and a Combination of MCT and PGMS The β-D-galactosidases which were micro-encapsulated with MCT in Example I, with PGMS in Example II and with a combination of MCT and PGMS in Example III, each was added to milk at an amount of 60 ppm and the milk was stored at 5° C. for 5 days. The off-flavor of the milk was compared with that of general milk. The result is given in Table 6, below. As shown in Table 6, 17 persons answered "the same as in general milk's" for the MCT-treated milk while 20 persons answered "the same as in general milk" for the PGMS-treated milk. In the case of the milk added with the β-D-galactosidase encapsulated with a combination of MCT and PGMS, 19 persons answered "the same" and one person "a little more off-flavored than general milk".

TABLE 6

Functional Test for Off-Flavor of Milk Containing the β-D-Galactosidase microencapsulated with a combination of MCT and PGMS

| Degree of Off-Flavor | Examinees[1] Milk with Microencapsulated Enz. | | |
|---|---|---|---|
| | MCT+ | PGMS | MCT + PGMS |
| The Same | 17 | 20 | 19 |
| A little more off-flavored | 3 | 0 | 1 |
| Moderately more off-flavored | 0 | 0 | 0 |
| Considerably more off-flavored | 0 | 0 | 0 |
| Much more off-flavored | 0 | 0 | 0 |

[1]20 persons in total

EXAMPLE VII

Clinical Demonstration of Milk Containing β-D-Galactosidase Encapsulated with MCT and PGMS to Milk-Intolerant Patient The β-D-galactosidases which were micro-encapsulated with MCT in Example I and with PGMS in example II, each was added to milk at an amount of 60 ppm and 200 ml of the milk was supplied to each of 20 patients who showed the clinical symptoms of lactose intolerance, such as abdominal distention, nausea, cramping, pain, and watery diarrhea, for clinical demonstration. After drinking, 13 patients answered "completely improved in lactose intolerance", 5 patients "considerably improved" and 2 patients "moderately improved". The result is given in Tale 7, below.

TABLE 7

Clinical Demonstration of the Milk to Milk-Intolerant patients

| Improvement | Examinees[1] |
|---|---|
| Never | 0 |
| A little improved | 0 |
| Moderately improved | 2 |
| Considerably improved | 5 |
| Much improved | 13 |

[1]20 persons in total

As described hereinbefore, the milk which contains the β-D-galactosidase micro-encapsulated with fatty acid ester, does not change in sweetness with storage, maintains its characteristic taste without off-flavor and is digestible to the β-D-galactosidase-deficient people, giving a medically meaningful advance to the milk product processing industry.

The present invention has been described in an illustrative manner, and it is to be understood the terminology used us intended to be in the nature of description rather than of limitation.

Many modifications and variations of the present invention are possible in light of the above teachings. Therefore, it is to be understood that within the scope of the appended claims, the invention may be practiced otherwise than as specifically described.

What is claimed is:

1. A microencapsulated β-D-galactosidase, in which a mixture of decaglycerin monostearate (PGMS) and distilled water at a ratio of 5:4 is used as a coating agent for microencapsulation, prepared by the steps of:

mixing and stirring the coating agent and β-D-galactosidase at a ratio in the range of 15:1 to 20:1;

spraying the mixture to a dispersant containing a fatty acid ester using a spray gun;

centrifuging the resulting solution;

mixing the supernatant and the dispersant with an equal volume; and centrifuging the resulting mixture.

2. Milk, which contains the microencapsulated β-D-galactosidase of claim 1.

3. In a material encapsulated with medium chain triglyceride (MCT) as a coating agent, a microencapsulated β-D-galactosidase prepared by the steps of:

mixing and stirring the coating agent and β-D-galactosidase at a ratio in the range of 15:1 to 20:1;

spraying the mixture to a dispersant containing a fatty acid ester using a spray gun;

centrifuging the resulting solution;

mixing the supernatant and the dispersant with an equal volume; and centrifuging the resulting mixture.

4. Milk, which contains the microencapsulated β-D-galactosidase of claim 3.

5. A microencapsulated β-D-galactosidase, in which a mixture of PGMS and MCT at a ratio of 5:5 is used as a coating agent for microencapsulation, prepared by the steps of:

mixing and stirring the coating agent and β-D-galactosidase at a ratio in the range of 15:1 to 20:1;

spraying the mixture to a dispersant containing a fatty acid ester using a spray gun;

centrifuging the resulting solution; mixing the supernatant and the dispersant with an equal volume; and centrifuging the resulting mixture.

6. Milk, which contains the microencapsulated β-D-galactosidase of claim 5.

* * * * *